United States Patent
Al-Ali

(10) Patent No.: US 10,433,776 B2
(45) Date of Patent: *Oct. 8, 2019

(54) LOW POWER PULSE OXIMETER

(71) Applicant: Masimo Corporation, Irvine, CA (US)

(72) Inventor: Ammar Al-Ali, Tustin, CA (US)

(73) Assignee: MASIMO CORPORATION, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/174,144

(22) Filed: Oct. 29, 2018

(65) Prior Publication Data

US 2019/0069814 A1 Mar. 7, 2019

Related U.S. Application Data

(63) Continuation of application No. 15/820,082, filed on Nov. 21, 2017, which is a continuation of application No. 13/908,957, filed on Jun. 3, 2013, now Pat. No. 9,848,806, which is a continuation of application No. 11/939,519, filed on Nov. 13, 2007, now Pat. No. 8,457,703, which is a continuation of application No. 10/785,573, filed on Feb. 24, 2004, now Pat. No. 7,295,866, which is a continuation of application No.

(Continued)

(51) Int. Cl.
   *A61B 5/1455* (2006.01)
(52) U.S. Cl.
   CPC ........ *A61B 5/1455* (2013.01); *A61B 5/14551* (2013.01); *A61B 2560/0209* (2013.01)
(58) Field of Classification Search
   CPC .. A61B 5/00; A61B 5/02; A61B 5/021; A61B 5/0205; A61B 5/03; A61B 5/04; A61B 5/0059; A61B 5/08; A61B 5/103; A61B 5/0093; A61B 5/68; A61B 5/145; A61B 5/1455; A61B 5/14551
   See application file for complete search history.

(56) References Cited

U.S. PATENT DOCUMENTS

| | | | |
|---|---|---|---|
| 4,907,183 A | * | 3/1990 | Tanaka ...................... G06F 1/30 365/229 |
| 4,960,128 A | | 10/1990 | Gordon et al. |
| 4,964,408 A | | 10/1990 | Hink et al. |

(Continued)

FOREIGN PATENT DOCUMENTS

| | | |
|---|---|---|
| EP | 0 872 210 A1 | 10/1998 |
| WO | WO 99/63883 | 12/1999 |

OTHER PUBLICATIONS

US 8,845,543 B2, 09/2014, Diab et al. (withdrawn)

(Continued)

*Primary Examiner* — Eric F Winakur
*Assistant Examiner* — Chu Chuan Liu
(74) *Attorney, Agent, or Firm* — Knobbe, Martens, Olson & Bear, LLP

(57) ABSTRACT

A pulse oximeter may reduce power consumption in the absence of overriding conditions. Various sampling mechanisms may be used individually or in combination. Various parameters may be monitored to trigger or override a reduced power consumption state. In this manner, a pulse oximeter can lower power consumption without sacrificing performance during, for example, high noise conditions or oxygen desaturations.

16 Claims, 11 Drawing Sheets

Related U.S. Application Data

10/184,028, filed on Jun. 26, 2002, now Pat. No. 6,697,658.

(60) Provisional application No. 60/302,564, filed on Jul. 2, 2001.

(56) References Cited

U.S. PATENT DOCUMENTS

| | | |
|---|---|---|
| 5,041,187 A | 8/1991 | Hink et al. |
| 5,069,213 A | 12/1991 | Polczynski |
| 5,069,214 A * | 12/1991 | Samaras ............ A61B 5/14551 600/323 |
| 5,163,438 A | 11/1992 | Gordon et al. |
| 5,238,001 A * | 8/1993 | Gallant ................ A61B 5/0205 600/513 |
| 5,279,298 A * | 1/1994 | Flower ................ A61B 3/1241 351/206 |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,490,523 A | 2/1996 | Isaacson et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,619,992 A | 4/1997 | Guthrie et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,746,694 A | 5/1998 | Wilk et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,797,841 A | 8/1998 | Delonzor et al. |
| 5,810,734 A | 9/1998 | Caro et al. |
| 5,823,950 A | 10/1998 | Diab et al. |
| 5,827,969 A | 10/1998 | Lee et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,924,979 A | 7/1999 | Swedlow et al. |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,622 A | 9/2000 | Minoz |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,270,460 B1 | 8/2001 | McCartan et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,396,137 B1 | 5/2002 | Klughart |
| 6,397,091 B2 | 5/2002 | Diab et al. |
| 6,402,690 B1 * | 6/2002 | Rhee ................... A61B 5/0002 600/300 |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,527,729 B1 | 3/2003 | Turcott |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B2 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |

(56) References Cited

U.S. PATENT DOCUMENTS

| | | |
|---|---|---|
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,190,986 B1 | 3/2007 | Hannula et al. |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |

(56) References Cited

U.S. PATENT DOCUMENTS

| | | |
|---|---|---|
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |

(56) References Cited

U.S. PATENT DOCUMENTS

| | | |
|---|---|---|
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |

(56) References Cited

U.S. PATENT DOCUMENTS

| | | |
|---|---|---|
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| D833,624 S | 11/2018 | DeJong et al. |
| 10,123,726 B2 | 11/2018 | Al-Ali et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Kiani et al. |
| 10,188,348 B2 | 1/2019 | Al-Ali et al. |
| RE47,218 E | 2/2019 | Ali-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 2003/0218386 A1 | 11/2003 | Dalke et al. |
| 2005/0234317 A1 | 10/2005 | Kiani |
| 2006/0094943 A1 | 5/2006 | Van Slyke |
| 2006/0161054 A1 | 7/2006 | Reuss et al. |
| 2007/0073121 A1 | 3/2007 | Hoarau et al. |
| 2007/0282478 A1 | 12/2007 | Al-Ali et al. |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2011/0001605 A1 | 1/2011 | Kiani et al. |
| 2011/0082711 A1 | 4/2011 | Poeze et al. |
| 2011/0087083 A1 | 4/2011 | Poeze et al. |
| 2011/0105854 A1 | 5/2011 | Kiani et al. |
| 2011/0125060 A1 | 5/2011 | Telfort et al. |
| 2011/0208015 A1 | 8/2011 | Welch et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2011/0237969 A1 | 9/2011 | Eckerbom et al. |
| 2011/0288383 A1 | 11/2011 | Diab |
| 2012/0041316 A1 | 2/2012 | Al-Ali et al. |
| 2012/0046557 A1 | 2/2012 | Kiani |
| 2012/0059267 A1 | 3/2012 | Lamego et al. |
| 2012/0088984 A1 | 4/2012 | Al-Ali et al. |
| 2012/0165629 A1 | 6/2012 | Merritt et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0262730 A1 | 10/2013 | Al-Ali et al. |
| 2013/0274572 A1 | 10/2013 | Al-Ali et al. |
| 2013/0296672 A1 | 11/2013 | O'Neil et al. |
| 2013/0296713 A1 | 11/2013 | Al-Ali et al. |
| 2013/0317370 A1 | 11/2013 | Dalvi et al. |
| 2013/0324808 A1 | 12/2013 | Al-Ali et al. |
| 2013/0331660 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0034353 A1 | 2/2014 | Al-Ali et al. |
| 2014/0051953 A1 | 2/2014 | Lamego et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |

(56) References Cited

U.S. PATENT DOCUMENTS

| | | |
|---|---|---|
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0276115 A1 | 9/2014 | Dalvi et al. |
| 2014/0288400 A1 | 9/2014 | Diab et al. |
| 2014/0303520 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2014/0357966 A1 | 12/2014 | Al-Ali et al. |
| 2014/0371548 A1 | 12/2014 | Al-Ali et al. |
| 2014/0378784 A1 | 12/2014 | Kiani et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0196249 A1 | 7/2015 | Brown et al. |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Kind et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0021099 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055847 A1 | 3/2017 | Kiani et al. |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |

(56) References Cited

U.S. PATENT DOCUMENTS

| | | |
|---|---|---|
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0076028 A1 | 3/2019 | Al-Ali et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |

OTHER PUBLICATIONS

US 9,579,050 B2, 02/2017, Al-Ali (withdrawn)

International Search Report dated Jul. 11, 2002, International Application No. PCT/US02/20675 filed Jun. 28, 2002.

U.S. Appl. No. 15/820,082, Low Power Pulse Oximeter, filed Nov. 21, 2017.

U.S. Appl. No. 16/174,130, Low Power Pulse Oximeter, filed Oct. 29, 2018.

Nov. 8, 2018 Complaint for (1) Breach of Contract (2) Trade Secret Misappropriation (3) Breach of Fiduciary Duty and (4) Patent Infringement and Demand for Jury Trial, *Masimo Corporation and Cercacor Laboratories, Inc. v. True Wearables, Inc. and Marcelo Lamego*, Case No. 8:18-cv-2001.

May 15, 2019 Defendants True Wearables, Inc.'s and Marcelo Lamego's Preliminary Invalidity Contentions, *Masimo Corporation and Cercacor Laboratories, Inc. v. True Wearables, Inc. and Marcelo Lamego*, Case No. 8:18-cv-2001-JVS-JDE.

New, William, Jr., "Continuous Non-Invasive Measurement of Arterial Oxygen", Journal of Japan Society for Clinical Anesthesia, vol. 6, No. 6, pp. 460-468 (Dec. 15, 1986).

\* cited by examiner

LOW POWER PULSE OXIMETER

REFERENCE TO RELATED APPLICATIONS

Any and all applications for which a foreign or domestic priority claim is identified in the Application Data Sheet as filed with the present application are incorporated by reference under 37 CFR 1.57 and made a part of this specification.

BACKGROUND OF THE INVENTION

Pulse oximetry is a widely accepted noninvasive procedure for measuring the oxygen saturation level of a person's arterial blood, an indicator of their oxygen supply. Oxygen saturation monitoring is crucial in critical care and surgical applications, where an insufficient blood supply can quickly lead to injury or death. FIG. 1 illustrates a conventional pulse oximetry system 100, which has a sensor 110 and a monitor 150. The sensor 110, which can be attached to an adult's finger or an infant's foot, has both red and infrared LEDs 112 and a photodiode detector 114. For a finger, the sensor is configured so that the LEDs 112 project light through the fingernail and into the blood vessels and capillaries underneath. The photodiode 114 is positioned at the finger tip opposite the fingernail so as to detect the LED emitted light as it emerges from the finger tissues. A pulse oximetry sensor is described in U.S. Pat. No. 6,088,607 entitled "Low Noise Optical Probe," which is assigned to the assignee of the present invention and incorporated by reference herein.

Also shown in FIG. 1, the monitor 150 has LED drivers 152, a signal conditioning and digitization front-end 154, a signal processor 156, a display driver 158 and a display 159. The LED drivers 152 alternately activate the red and IR LEDs 112 and the front-end 154 conditions and digitizes the resulting current generated by the photodiode 114, which is proportional to the intensity of the detected light. The signal processor 156 inputs the conditioned photodiode signal and determines oxygen saturation based on the differential absorption by arterial blood of the two wavelengths emitted by the LEDs 112. Specifically, a ratio of detected red and infrared intensities is calculated by the signal processor 156, and an arterial oxygen saturation value is empirically determined based on the ratio obtained. The display driver 158 and associated display 159 indicate a patient's oxygen saturation, heart rate and plethysmographic waveform.

SUMMARY OF THE INVENTION

Increasingly, pulse oximeters are being utilized in portable, battery-operated applications. For example, a pulse oximeter may be attached to a patient during emergency transport and remain with the patient as they are moved between hospital wards. Further, pulse oximeters are often implemented as plug-in modules for multiparameter patient monitors having a restricted power budget. These applications and others create an increasing demand for lower power and higher performance pulse oximeters. A conventional approach for reducing power consumption in portable electronics, typically utilized by devices such as calculators and notebook computers, is to have a "sleep mode" where the circuitry is powered-down when the devices are idle.

FIG. 2 illustrates a sleep-mode pulse oximeter 200 utilizing conventional sleep-mode power reduction. The pulse oximeter 200 has a pulse oximeter processor 210 and a power control 220. The power control 220 monitors the pulse oximeter output parameters 212, such as oxygen saturation and pulse rate, and controls the processor power 214 according to measured activity. For example, if there is no significant change in the oxygen saturation value over a certain time period, the power control 220 will power down the processor 210, except perhaps for a portion of memory. The power control 220 may have a timer that triggers the processor 210 to periodically sample the oxygen saturation value, and the power control 220 determines if any changes in this parameter are occurring. If not, the power control 220 will leave the processor 210 in sleep mode.

There are a number of disadvantages to applying consumer electronic sleep mode techniques to pulse oximetry. By definition, the pulse oximeter is not functioning during sleep mode. Unlike consumer electronics, pulse oximetry cannot afford to miss events, such as patient oxygen desaturation. Further, there is a trade-off between shorter but more frequent sleep periods to avoid a missed event and the increased processing overhead to power-up after each sleep period. Also, sleep mode techniques rely only on the output parameters to determine whether the pulse oximeter should be active or in sleep mode. Finally, the caregiver is given no indication of when the pulse oximeter outputs were last updated.

One aspect of a low power pulse oximeter is a sensor interface adapted to drive a pulse oximetry sensor and receive a corresponding input signal. A processor derives a physiological measurement corresponding to the input signal, and a display driver communicates the measurement to a display. A controller generates a sampling control output to at least one of said sensor interface and said processor so as to reduce the average power consumption of the pulse oximeter consistent with a predetermined power target.

In one embodiment, a calculator derives a signal status output responsive to the input signal. The signal status output is communicated to the controller to override the sampling control output. The signal status output may indicate the occurrence of a low signal quality or the occurrence of a physiological event. In another embodiment, the sensor interface has an emitter driver adapted to provide a current output to an emitter portion of the sensor. Here, the sampling control output determines a duty cycle of the current output. In a particular embodiment, the duty cycle may be in the range of about 3.125% to about 25%.

In another embodiment, the sensor interface has a front-end adapted to receive the input signal from a detector portion of the sensor and to provide a corresponding digitized signal. Here, the sampling control output determines a powered-down period of the front-end. A confidence indicator responsive to a duration of the powered-down period may be provided and displayed.

In yet another embodiment, the pulse oximeter comprises a plurality of data blocks responsive to the input signal, wherein the sampling control output determines a time shift of successive ones of the data blocks. The time shift may vary in the range of about 1.2 seconds to about 4.8 seconds.

An aspect of a low power pulse oximetry method comprises the steps of setting a power target and receiving an input signal from a pulse oximetry sensor. Further steps include calculating signal status related to the input signal, calculating power status related to the power target, and sampling based upon the result of the calculating signal status and the calculating power status steps.

In one embodiment, the calculating signal status step comprises the substeps of receiving a signal statistic related to the input signal, receiving a physiological measurement related to the input signal, determining a low signal quality condition from the signal statistic, determining an event occurrence from the physiological measurement, and indicating an override based upon the low signal quality condition or the event occurrence. The calculating power status step may comprise the substeps of estimating an average power consumption for at least a portion of the pulse oximeter, and indicating an above power target condition when the average power consumption is above the power target. The sampling step may comprise the substep of increasing sampling as the result of the override. The sampling step may also comprise the substep of decreasing sampling as the result of the above power target condition, except during the override.

Another aspect of a low power pulse oximetry method comprises the steps of detecting an override related to a measure of signal quality or a physiological measurement event, increasing the pulse oximeter power to a higher power level when the override exists, and reducing the pulse oximeter power to a lower power level when the override does not exist. The method may comprise the further steps of predetermining a target power level for a pulse oximeter and cycling between the lower power level and the higher power level so that an average pulse oximeter power is consistent with the target power level.

In one embodiment, the reducing step comprises the substep of decreasing the duty cycle of an emitter driver output to the sensor. In another embodiment, the reducing step comprises the substep of powering-down a detector front-end. A further step may comprise displaying a confidence indicator related to the duration of the powering-down substep. In yet another embodiment, the reducing step comprises the substep of increasing the time-shift of post-processor data blocks.

Another aspect of a low power pulse oximeter comprises a sensor interface adapted to receive an input signal from a sensor, a signal processor configured to communicate with the sensor interface and to generate an internal parameter responsive to the input signal, and a sampling controller responsive to the internal parameter so as to generate a sampling control to alter the power consumption of at least one of the sensor interface and the signal processor. The signal processor may be configured to generate an output parameter and the sampling controller may be responsive to a combination of the internal and output parameters so as to generate a sampling control to alter the power consumption of at least one of the sensor interface and the signal processor. The internal parameter may be indicative of the quality of the input signal. The output parameter may be indicative of oxygen saturation.

In another embodiment, the sampling controller is responsive to a predetermined power target in combination with the internal parameter so as to generate a sampling control to alter the power consumption of at least one of the sensor interface and the signal processor. The signal processor may be configured to generate an output parameter and the sampling controller may be responsive to a combination of the internal and output parameters and the power target so as to generate a sampling control to alter the power consumption of at least one of the sensor interface and the signal processor. The sensor interface may comprise an emitter driver and the sampling control may modify a duty cycle of the emitter driver. The sensor interface may comprise a detector front-end and the sampling control may intermittently power-down the detector front-end. The processor may generate a plurality of data blocks corresponding to the input signal, where each of the data blocks have a time shift from a preceding one of the data blocks, and where the sampling control may determine the amount of the time shift.

A further aspect of a low power pulse oximeter comprises an interface means for communicating with a sensor, a processor means for generating an internal parameter and an output parameter, and a controller means for selectively reducing the power consumption of at least one of the interface means and the processor means based upon the parameters. In one embodiment, the interface means comprises a driver means for determining the duty cycle of emitter current to the sensor, the driver means being responsive to the controller means. In another embodiment, the interface means comprises a detector front-end means for receiving an input signal from the sensor, the power for the detector front-end means being responsive to the controller means. In yet another embodiment, the processor means comprises a post-processor means for determining a time shift between data blocks, the post-processor means being responsive to the controller means. In a further embodiment, the controller means comprises a signal status calculator means for generating an indication of a low signal quality or a physiological event based upon at least one of an internal signal statistic and an output physiological measurement, and a control engine means in communications with the signal status calculator means for generating a sampling control responsive to the indication. In yet a further embodiment, the controller means comprises a power status calculator means for generating a power indication of power consumption relative to a power target, and a control engine means in communications with the power status calculator means for generating a sampling control responsive to the power indication.

DETAILED DESCRIPTION OF THE PREFERRED EMBODIMENT

Figure 1:
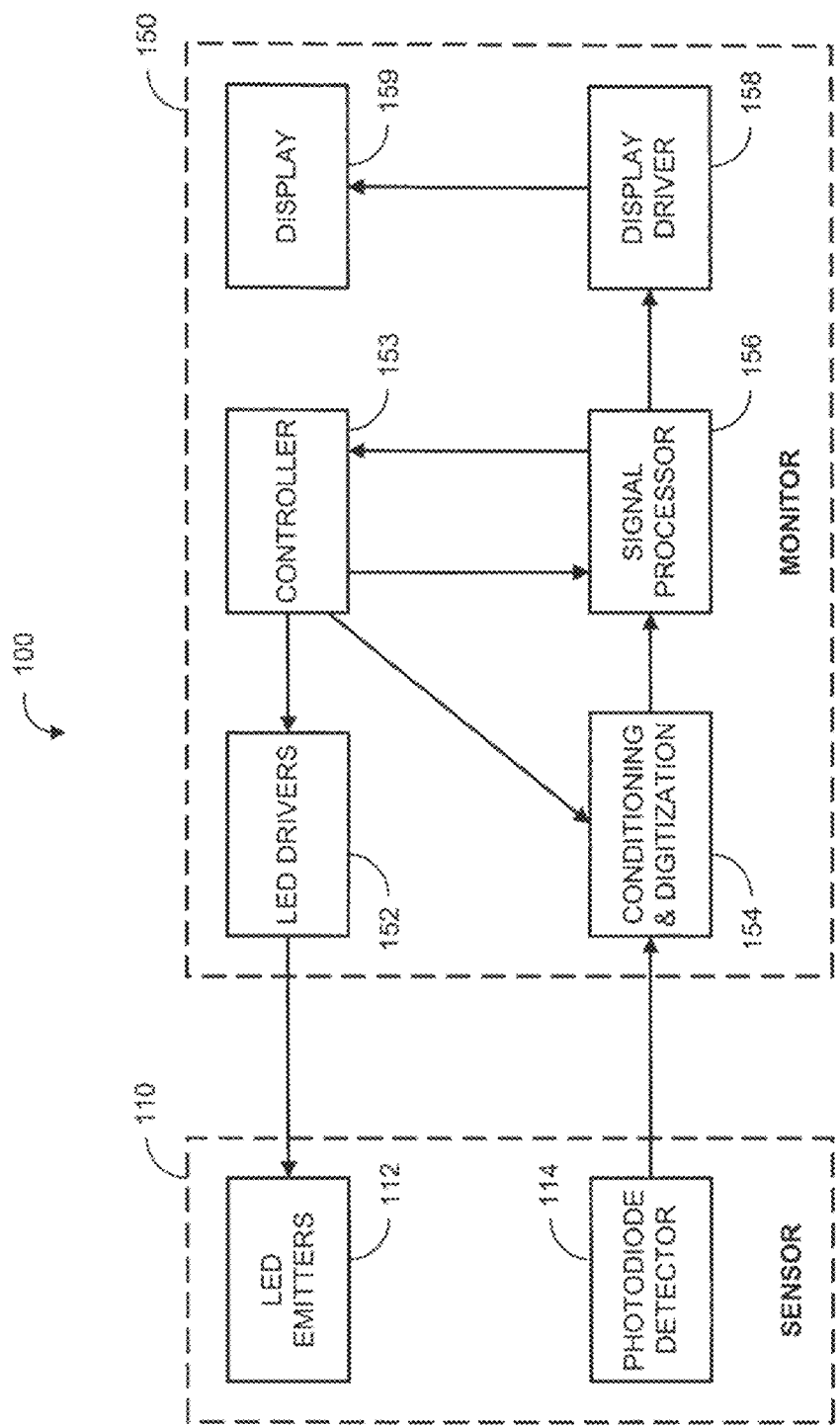
FIG. 1 is a block diagram of a conventional pulse oximeter sensor and monitor.
Figure 2:
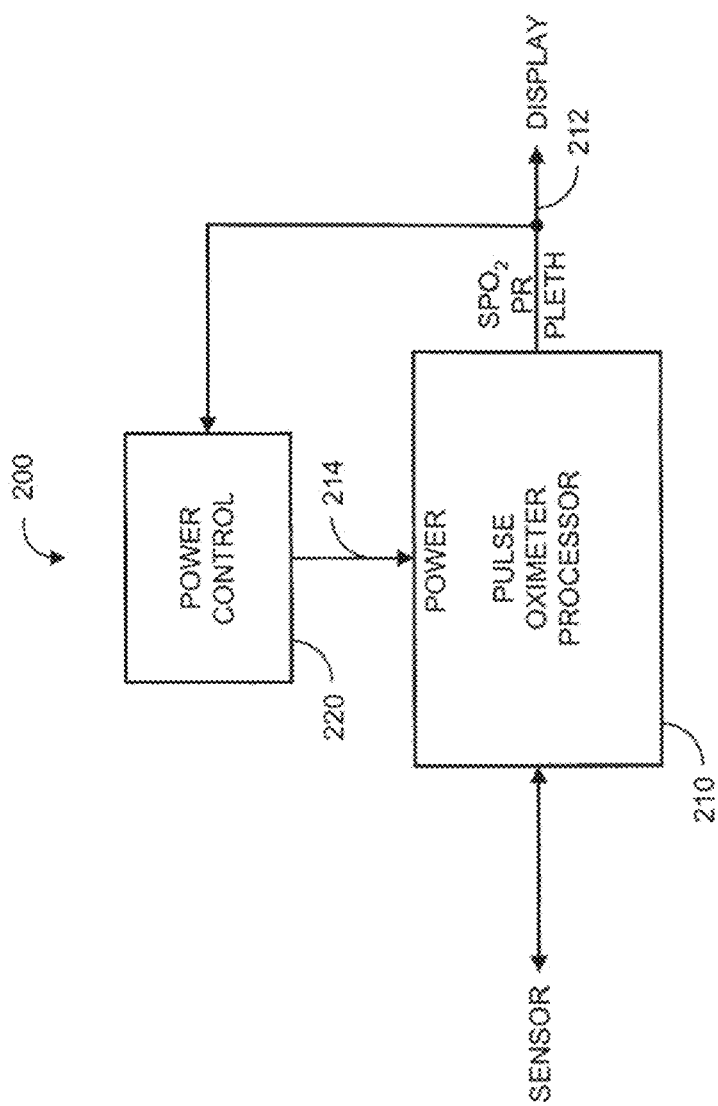
FIG. 2 is a block diagram of a pulse oximeter having a conventional sleep mode.
Figure 3:
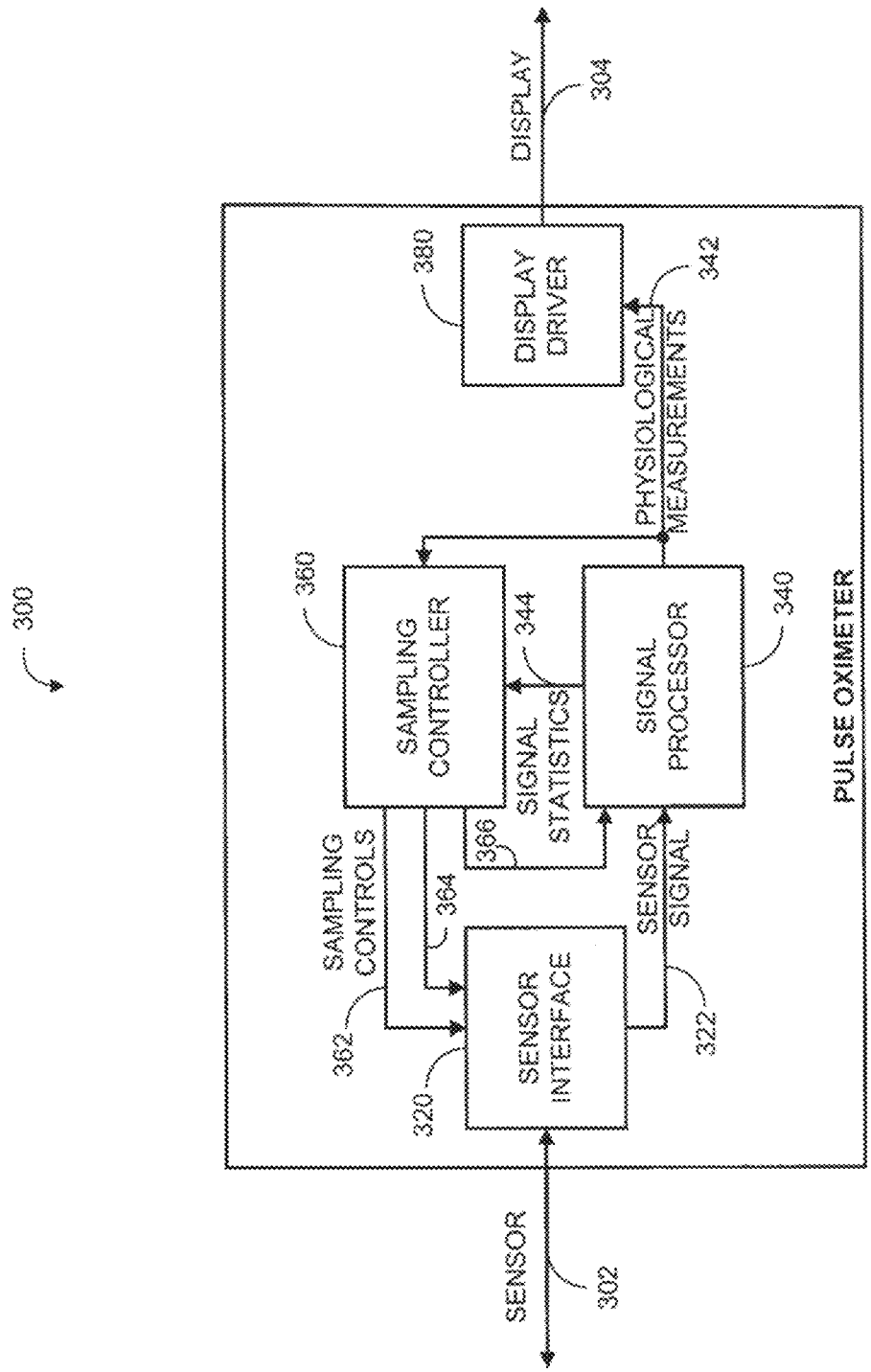
FIG. 3 is a top-level block diagram of a low power pulse oximeter.

FIG. 3 illustrates one embodiment of a low power pulse oximeter. The pulse oximeter 300 has a sensor interface 320, a signal processor 340, a sampling controller 360 and a display driver 380. The pulse oximeter 300 also has a sensor port 302 and a display port 304. The sensor port 302 connects to an external sensor, e.g. sensor 110 (FIG. 1). The sensor interface 320 drives the sensor port 302, receives a corresponding input signal from the sensor port 302, and provides a conditioned and digitized sensor signal 322 accordingly. Physiological measurements 342 are input to a display driver 380 that outputs to the display port 304. The display port 304 connects to a display device, such as a CRT or LCD, which a healthcare provider typically uses for monitoring a patient's oxygen saturation, pulse rate and plethysmograph.

As shown in FIG. 3, the signal processor 340 derives the physiological measurements 342, including oxygen saturation, pulse rate and plethysmograph, from the input signal 322. The signal processor 340 also derives signal statistics 344, such as signal strength, noise and motion artifact. The physiological measurements 342 and signal statistics 344 are input to the sampling controller 360, which outputs sampling controls 362, 364, 366 accordingly. The sampling controls 362, 364, 366 regulate pulse oximeter power dissipation by causing the sensor interface 320 to vary the sampling characteristics of the sensor port 302 and by causing the signal processor 340 to vary its sample processing characteristics, as described in further detail with respect to FIG. 4, below. Advantageously, power dissipation is responsive not only to output parameters, such as the physiological measurements 342, but also to internal parameters, such as the signal statistics 344.

Figure 4:
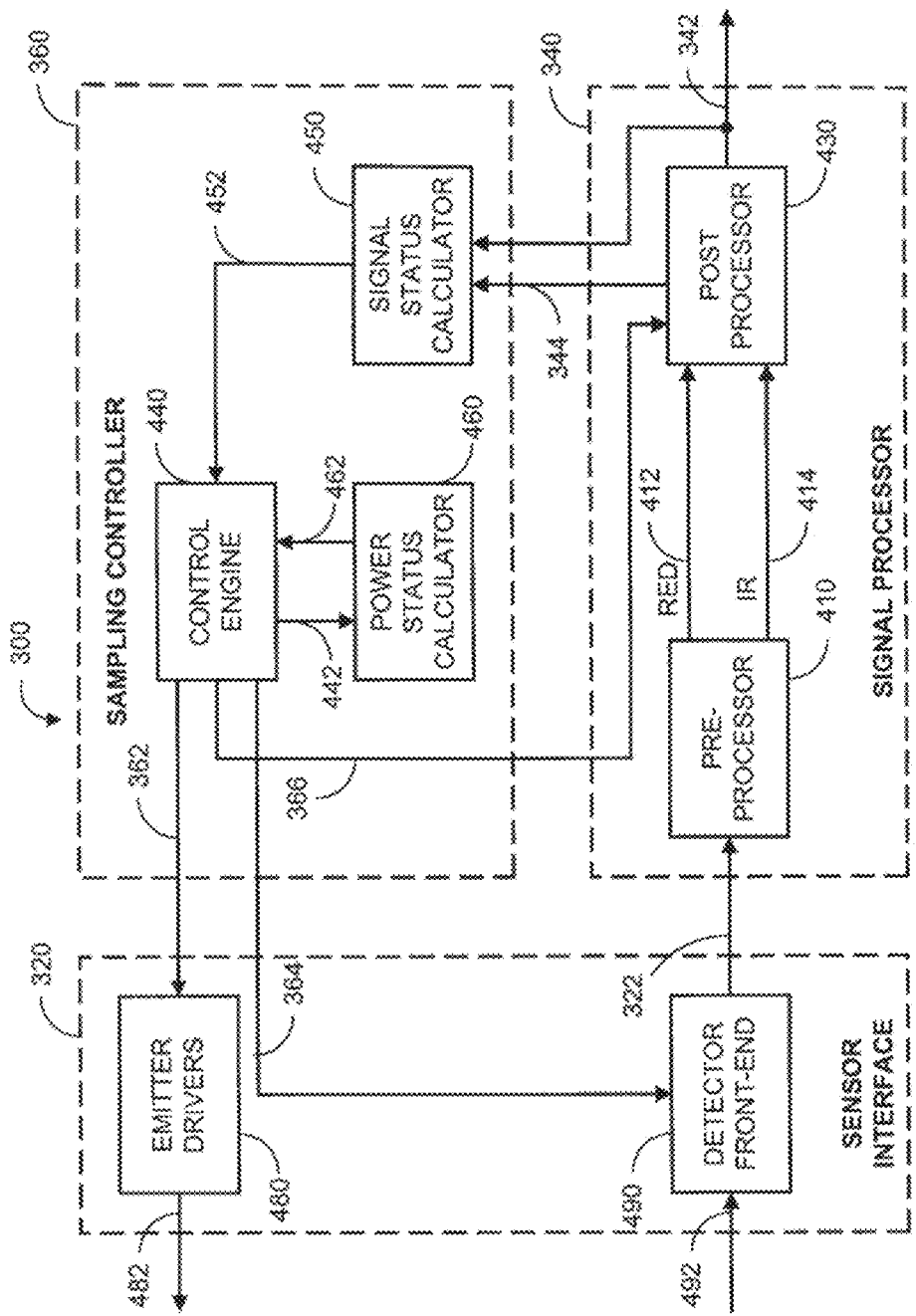
FIG. 4 is a detailed block diagram of a low power pulse oximeter illustrating a sensor interface, a signal processor and a sampling controller.

FIG. 4 illustrates further detail regarding the sensor interface 320, the signal processor 340 and the sampling controller 360. The sensor interface 320 has emitter drivers 480 and a detector front-end 490. The emitter drivers 480 are responsive to a sampling control 362, described below, and provide emitter drive outputs 482. The emitter drive outputs 482 activate the LEDs of a sensor attached to the sensor port 302 (FIG. 3). The detector front-end 490 receives an input signal 492 from a sensor attached to the sensor port 302 (FIG. 3) and provides a corresponding conditioned and digitized input signal 322 to the signal processor 340. A sampling control 364 controls power to the detector front-end 490, as described below.

As shown in FIG. 4, the signal processor 340 has a pre-processor 410 and a post processor 430. The pre-processor 410 demodulates red and IR signals from the digitized signal 322, performs filtering, and reduces the sample rate. The pre-processor provides a demodulated output, having a red channel 412 and an IR channel 414, which is input into the post-processor 430. The post processor 430 calculates the physiological measurements 342 and the signal statistics 344, which are output to a signal status calculator 450. The physiological measurements 342 are also output to a display driver 380 (FIG. 3) as described above. A pulse oximetry signal processor is described in U.S. Pat. No. 6,081,735 entitled "Signal Processing Apparatus," which is assigned to the assignee of the present invention and incorporated by reference herein.

Also shown in FIG. 4, the sampling controller 360 has a control engine 440, a signal status calculator 450 and a power status calculator 460. The control engine 440 outputs sampling controls 362, 364, 366 to reduce the power consumption of the pulse oximeter 300. In one embodiment, the control engine 440 advantageously utilizes multiple sampling mechanisms to alter power consumption. One sampling mechanism is an emitter duty cycle control 362 that is an input to the emitter drivers 480. The emitter duty cycle control 362 determines the duty cycle of the current supplied by the emitter drive outputs 482 to both red and IR sensor emitters, as described with respect to FIG. 5, below. Another sampling mechanism is a front-end control 364 that intermittently removes power to the detector front-end 490, as described with respected to FIG. 6, below. Yet another sampling mechanism is a data block overlap control 366 that varies the number of data blocks processed by the post processor 430. These various sampling mechanisms provide the flexibility to reduce power without sacrificing performance during, for example, high noise conditions or oxygen desaturation events, as described below in further detail.

The sampling controls 362, 364, 366 modify power consumption by, in effect, increasing or decreasing the number of input samples received and processed. Sampling, including acquiring input signal samples and subsequent sample processing, can be reduced during high signal quality periods and increased during low signal quality periods or when critical measurements are necessary. In this manner, the control engine 440 regulates power consumption to satisfy a predetermined power target, to minimize power consumption, or to simply reduce power consumption, as described with respect to FIGS. 8 and 10, below. The current state of the control engine is provided as a control state output 442 to the power status calculator 460. The control engine 440 utilizes the power status output 462 and the signal status output 452 to determine its next control state, as described with respect to FIGS. 9 and 11, below.

Further shown in FIG. 4, the signal status calculator 450 receives physiological measurements and signal statistics from the post processor 430 and determines the occurrence of an event or a low signal quality condition. An event determination is based upon the physiological measurements output 342 and may be any physiological-related indication that justifies the processing of more sensor samples and an associated higher power consumption level, such as an oxygen desaturation, a fast or irregular pulse rate or an unusual plethysmograph waveform to name a few. A low signal quality condition is based upon the signal statistics output 344 and may be any signal-related indication that justifies the processing of more sensor samples and an associated higher power consumption level, such as a low signal level, a high noise level or motion artifact to name a few. The signal status calculator 450 provides the signal status output 452 that is input to the control engine 440.

In addition, FIG. 4 shows that the power status calculator 460 has a control state input 442 and a power status output 462. The control state input 442 indicates the current state of the control engine 440. The power status calculator 460 utilizes an internal time base, such as a counter, timer or real-time clock, in conjunction with the control engine state to estimate the average power consumption of at least a portion of the pulse oximeter 300. The power status calculator 460 also stores a predetermined power target and compares its power consumption estimate to this target. The power status calculator 460 generates the power status output 462 as an indication that the current average power estimate is above or below the power target and provides this output 462 to the control engine 440.

Figure 5:
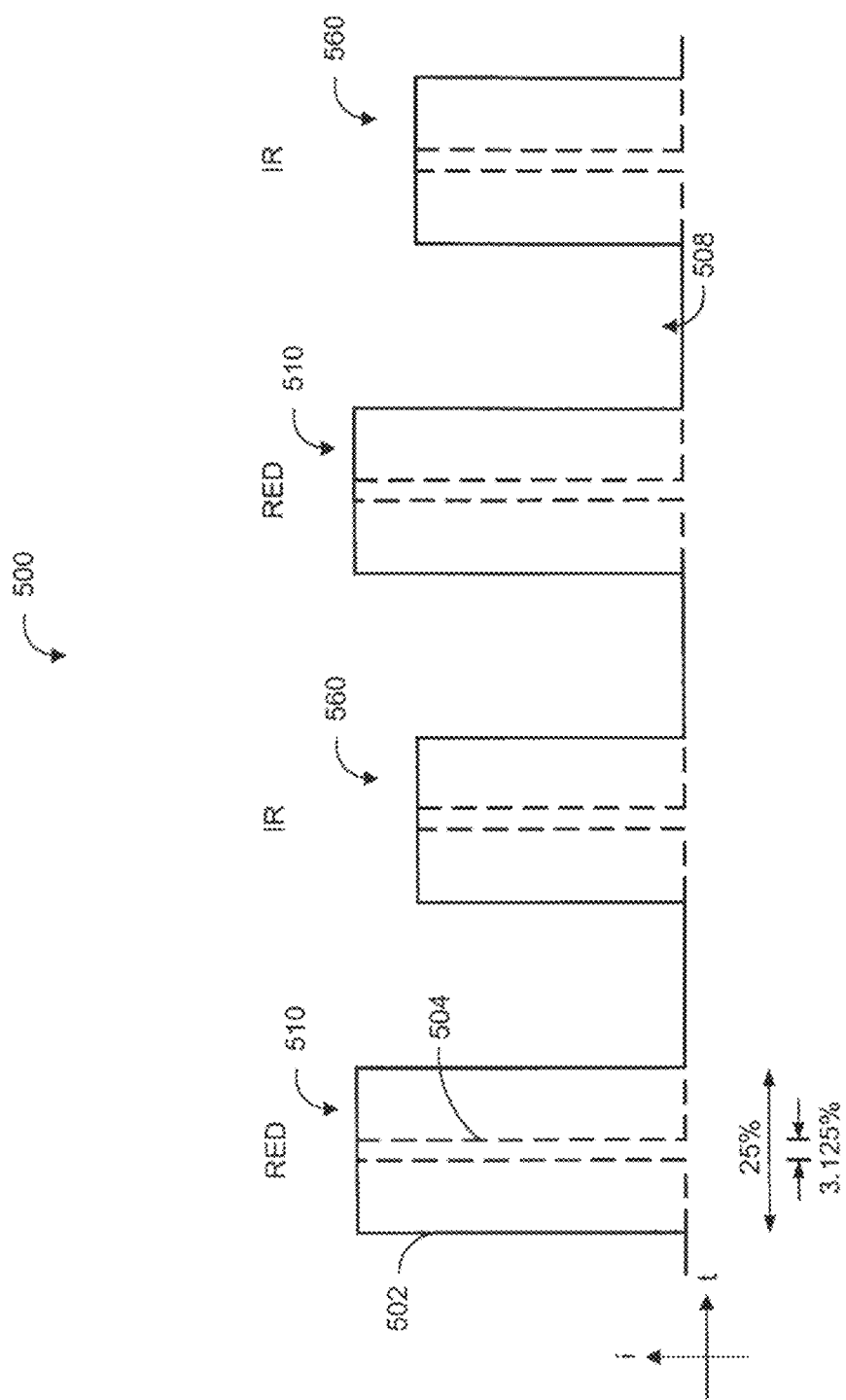
FIG. 5 is a graph of emitter drive current versus time illustrating variable duty cycle processing.

FIG. 5 illustrates emitter driver output current versus time. The graph 500 depicts the combination of a red LED drive current 510 and an IR drive current 560. The solid line graph 502 illustrates drive currents having a high duty cycle. The dashed line graph 504 illustrates drive currents having a low duty cycle. In a typical pulse oximeter, the duty cycle of the drive signals is constant and provides sufficient dark bands 508 to demodulate the detector response into red and IR channels. The emitter drivers 480 (FIG. 4), however, require a significant portion of the overall pulse oximeter power budget. Intermittently reducing the drive current duty cycle can advantageously reduce power dissipation without compromising signal integrity. As an example, a low power pulse oximeter implementation nominally consuming 500 mw may be able to reduce power consumption on the order of 70 mw by such drive current duty cycle reductions. In a preferred embodiment, the drive current duty cycle is varied within a range from about 25% to about 3.125%. In a more preferred embodiment, the drive current duty cycle is intermittently reduced from about 25% to about 3.125%. In conjunction with an intermittently reduced duty cycle or as an independent sampling mechanism, there may be a "data off" time period longer than one drive current cycle where the emitter drivers 480 (FIG. 4) are turned off. The detector front-end 490 (FIG. 4) may also be powered down during such a data off period, as described with respect to FIGS. 8 and 9, below.

Figure 6:
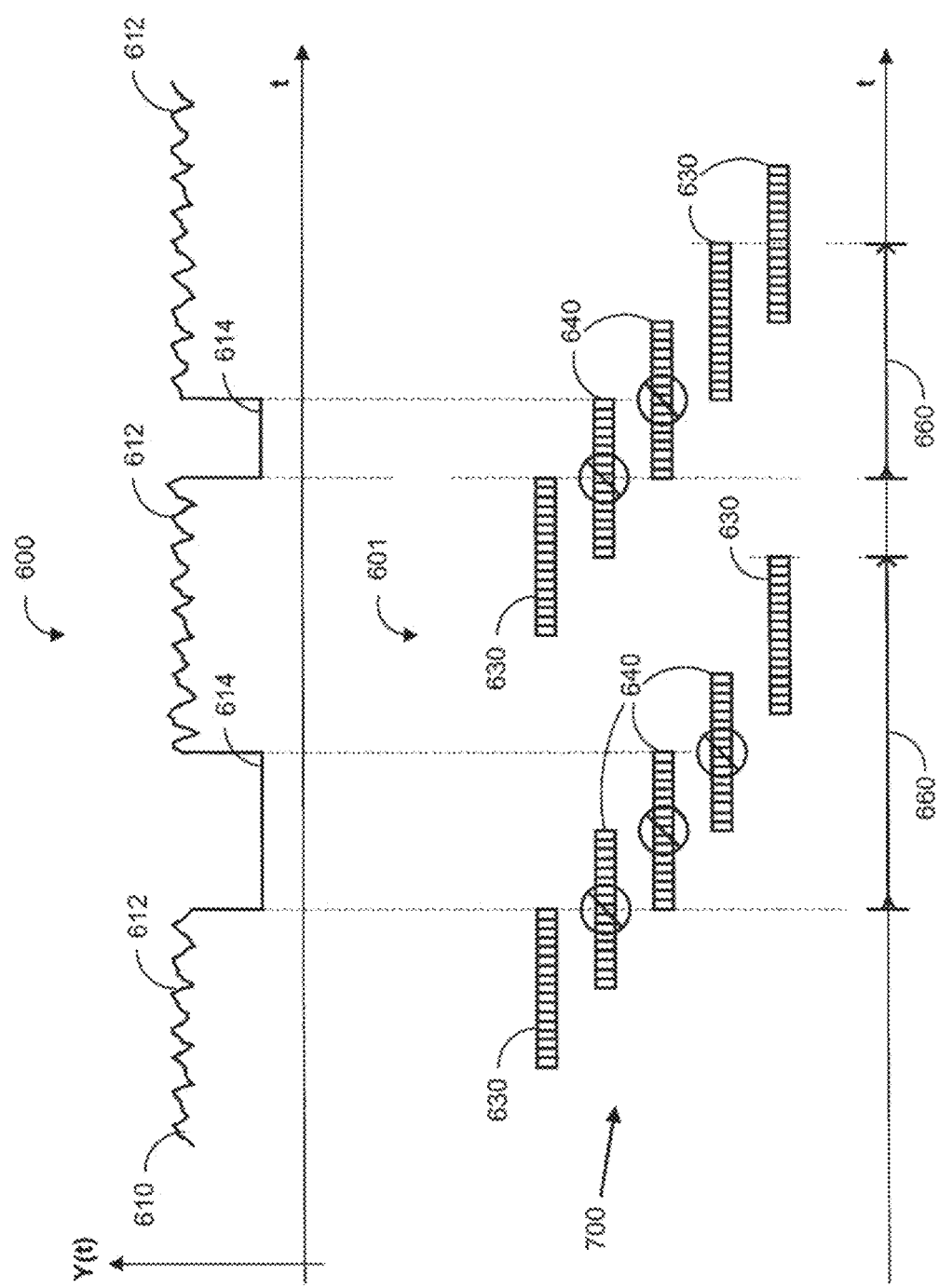
FIG. 6 is a graph of oxygen saturation versus time illustrating intermittent sample processing.

FIG. 6 is a graph 600 of a pre-processor output signal 610 over time depicting the result of intermittent sampling at the detector front-end 490 (FIG. 4). The output signal 610 is a red channel 412 (FIG. 4) or an IR channel 414 (FIG. 4) output from the pre-processor 410 (FIG. 4), which is input to the post processor 430 (FIG. 4), as described above. The output signal 610 has "on" periods 612, during which time the detector front-end 490 (FIG. 4) is powered-up and "off" periods 614, during which time the detector front-end 490 (FIG. 4) is powered-down. The location and duration of the on periods 612 and off periods 614 are determined by the front-end control 364 (FIG. 4).

Also shown in FIG. 6 is a corresponding timeline 601 of overlapping data blocks 700, which are "snap-shots" of the pre-processor output signal 610 over specific time intervals. Specifically, the post processor 430 (FIG. 4) processes a sliding window of samples of the pre-processor output signal 610, as described with respect to FIGS. 7A-B, below. Advantageously, the post processor 430 (FIG. 4) continues to function during off portions 614, marking as invalid those data blocks 640 that incorporate off portions 614. A freshness counter can be used to measure the time period 660 between valid data blocks 630, which can be displayed on a pulse oximeter monitor as an indication of confidence in the current measurements.

Figure 7:
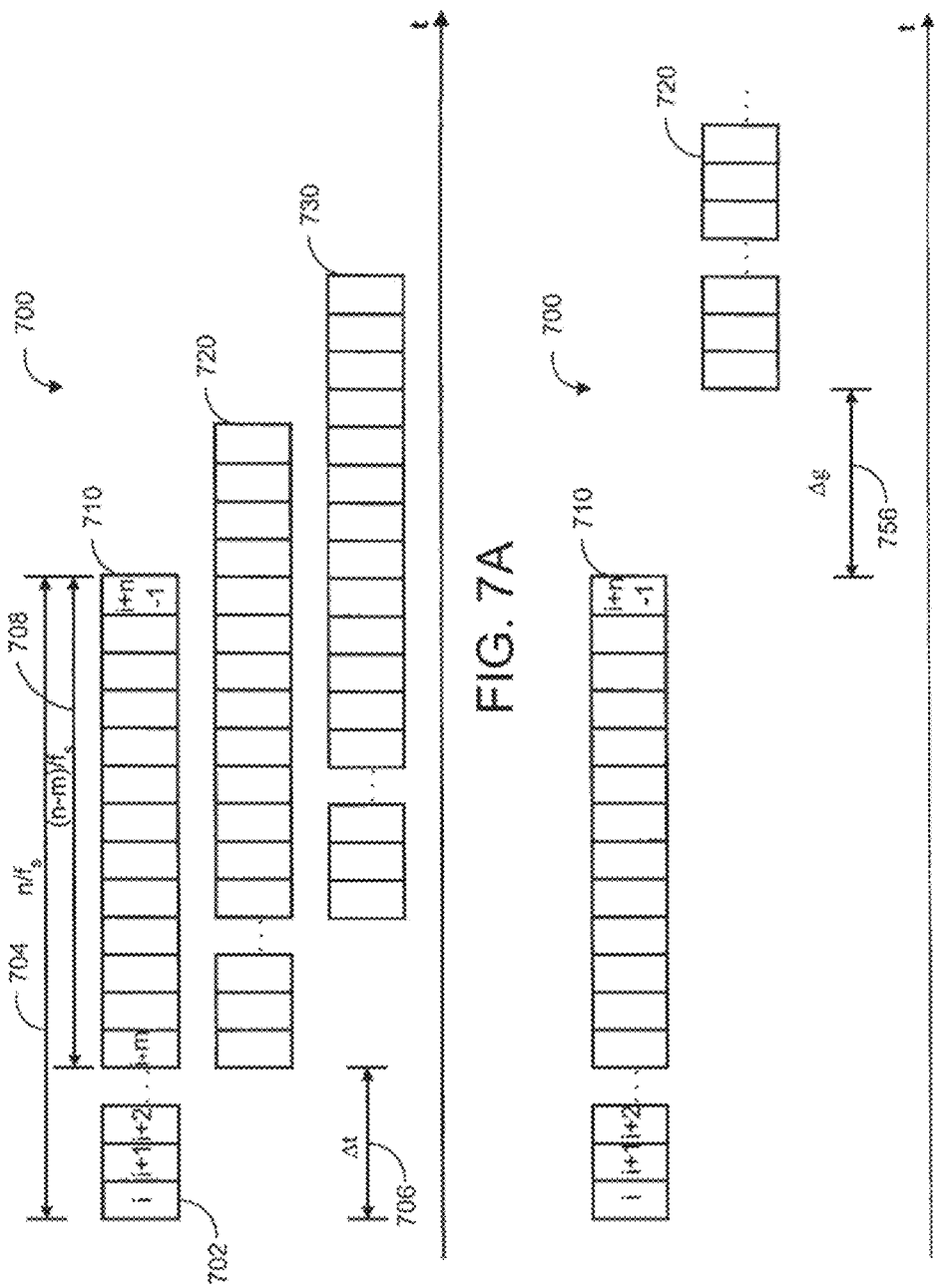
FIGS. 7A-B are graphs of data buffer content versus time illustrating variable data block overlap processing.

FIGS. 7A-B illustrate data blocks 700, which are processed by the post processor 430 (FIG. 4). Each data block 700 has n samples 702 of the pre-processor output and corresponds to a time interval 704 of $n/f_s$, where $f_s$ is the sample frequency. For example, in one embodiment n=600 and $f_s$=62.5 Hz. Hence, each data block time interval 704 is nominally 9.6 sec.

As shown in FIG. 7A, each data block 700 also has a relative time shift 706 from the preceding data block, where is an integral number of sample periods. That is, $=m/f_s$, where m is an integer representing the number of samples dropped from the preceding data block and added to the succeeding data block. In the embodiment described above, m=75 and =1.2 sec, nominally. The corresponding overlap 708 of two adjacent data blocks 710, 720 is $(n-m)/f_s$. In the embodiment described above, the overlap 708 is nominally 9.6 sec−1.2 sec=8.4 sec. The greater the overlap 708, i.e. the smaller the time shift 706, the more data blocks there are to process in the post-processor 430 (FIG. 4), with a corresponding greater power consumption. The overlap 708 between successive data blocks 710, 720 may vary from n−1 samples to no samples, i.e. no overlap. Also, as shown in FIG. 7B, there may be a sample gap 756 or negative overlap, i.e. samples between data blocks that are not processed by the post-processor, allowing further post-processor power savings. Sample gaps 756 may correspond to detector front-end off periods 614 (FIG. 6).

Figure 8:
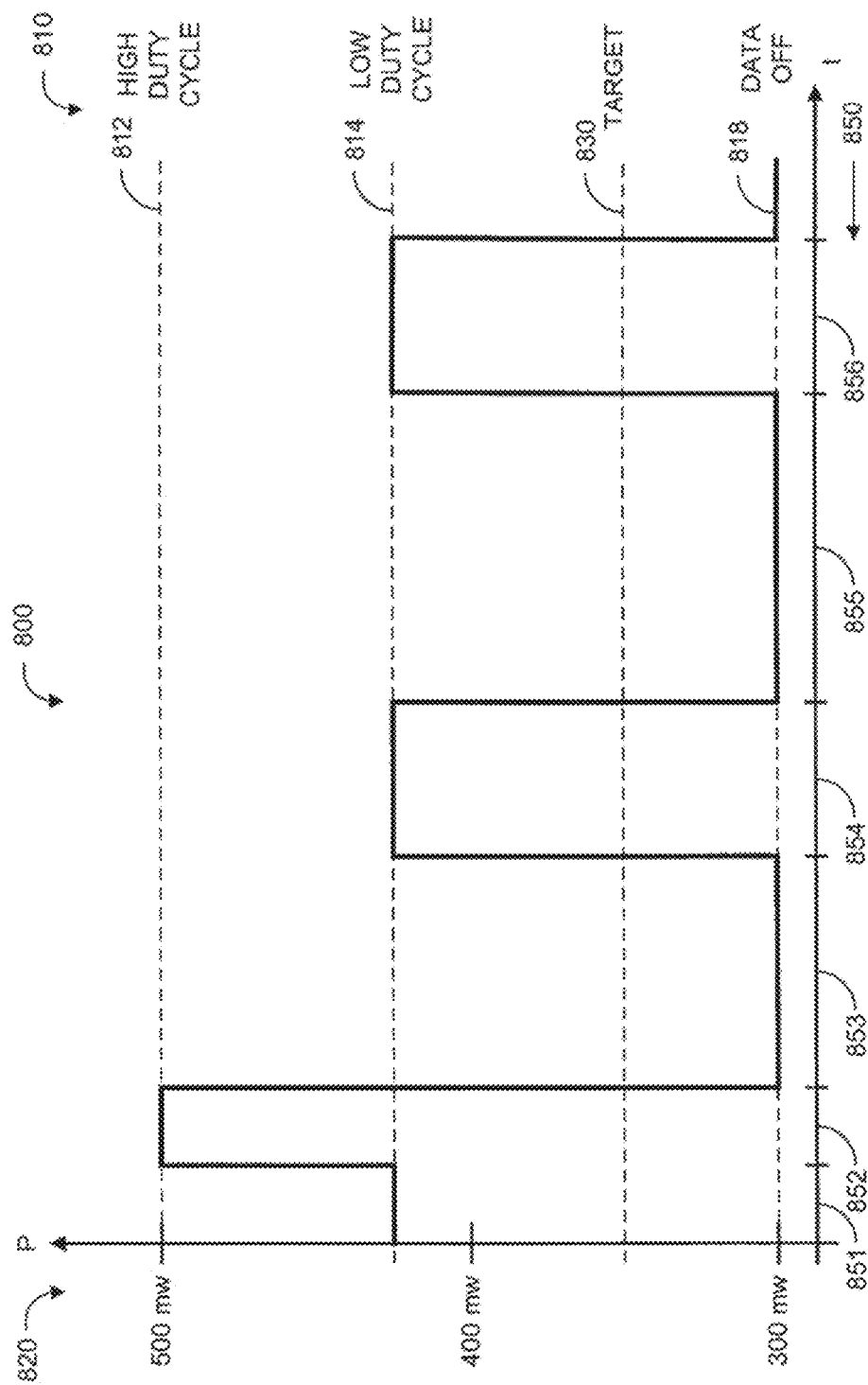
FIG. 8 is a graph of power versus time illustrating power dissipation conformance to an average power target using variable duty cycle and intermittent sample processing.

FIG. 8 illustrates an exemplar power consumption versus time profile 800 for the pulse oximeter 300 (FIG. 3) during various control engine states. In one embodiment, the control engine 440 (FIG. 4) has three states related to the sampling control outputs 362, 364 that affect pulse oximeter power consumption accordingly. One of ordinary skill in the art will recognize that the control engine 440 (FIG. 4) may have greater or fewer states and associated power consumption levels. The profile 800 shows the three control engine states 810 and the associated power consumption levels 820. These three states are high duty cycle 812, low duty cycle 814 and data off 818.

In the high duty cycle state 812, the control engine 440 (FIG. 4) causes the emitter drivers 480 (FIG. 4) to turn on sensor emitters for a relatively long time period, such as 25% on time for each of the red 510 and IR 560 drive currents. In the low duty cycle state 814, the control engine 440 (FIG. 4) causes the emitter drivers 480 (FIG. 4) to turn on sensor emitters for a relatively short time period, such as 3.125% of the time for each of the red 510 and IR 560 drive currents. In the data off state 818, the control engine 440 (FIG. 4) turns off the emitter drivers 480 (FIG. 4) and powers down the detector front-end 490 (FIG. 4). Also shown is a predetermined target power consumption level 830. The control engine 440 (FIG. 4) alters the sensor sampling of the pulse oximeter 300 (FIG. 3) so that the average power consumption matches the target level 830, as indicated by the power status output 462 (FIG. 4), except when overridden by the signal status output 452 (FIG. 4).

As shown in FIG. 8, power consumption changes according to the control states 810 during each of the time intervals 850. In a first time interval 851, the pulse oximeter is in a low duty cycle state 814 and transitions to a high duty cycle state 812 during a second time interval 852 due to an event or low quality signal. During a third time interval 853, the pulse oximeter is able to enter the data off state 818, during which time no sensor samples are processed. In a forth time interval 854, sensor samples are again taken, but at a low duty cycle 814. During the fifth and sixth time intervals 855, 856, sensor samples are shut off and turned on again as the pulse oximeter 300 (FIG. 3) alternates between the data off state 818 and the low duty cycle state 814 so as to maintain an average power consumption at the target level 830.

Figure 9:
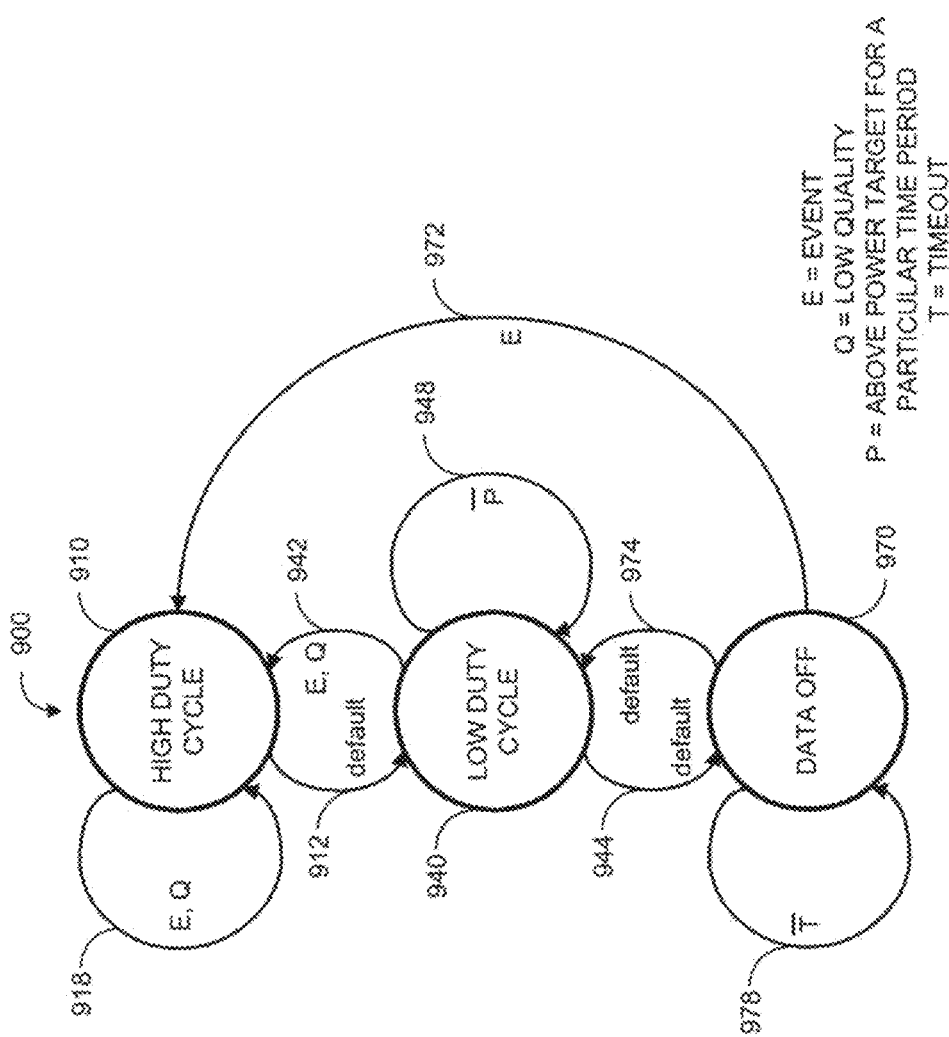
FIG. 9 is a state diagram of the sampling controller for variable duty cycle and intermittent sample processing.

FIG. 9 illustrates a state diagram 900 for one embodiment of the control engine 440 (FIG. 4). In this embodiment, there are three control states, high duty cycle 910, low duty cycle 940 and data off 970, as described with respect to FIG. 8, above. If the control state is data off 970, an event triggers a data-off to high-duty-cycle transition 972. If the control state is low duty cycle 940, an event similarly triggers a low-duty cycle to high-duty-cycle transition 942. In this manner, the occurrence of an event initiates high duty sensor sampling, allowing high fidelity monitoring of the event. Similarly, if the control state is low duty cycle 940, low signal quality triggers a low-duty cycle to high-duty-cycle transition 942. In this manner, low signal quality initiates higher duty sensor sampling, providing, for example, a larger signal-to-noise ratio.

Also shown in FIG. 9, if the control state is high duty cycle 910 and either an event is occurring or signal quality is low, then a null transition 918 maintains the high duty cycle state 910. If the pulse oximeter is not above the power target for more than a particular time interval, a null transition 948 maintains the low duty cycle state 940, so that sampling is turned-off only when necessary to track the power target. Further, if the control state is data off 970 and no time-out has occurred, a null transition 978 maintains the data off state 970, providing a minimum power consumption.

In addition, FIG. 9 shows that when the control state is in a high duty cycle state 910, if neither an event nor low signal quality are occurring, then a high-duty-cycle to low-duty-cycle transition 912 occurs by default. Also, if the control state is low duty cycle 940, if neither an event nor low signal quality are occurring and the power consumption is above the target level for longer than a particular time interval, a low-duty-cycle to data-off transition 944 occurs by default, allowing power consumption to come down to the target level. Further, if the control state is data off 970, if no event occurs and a timeout does occur, a data-off to low-duty-cycle transition 974 occurs by default, preventing excessively long periods of no sensor sampling.

Figure 10:
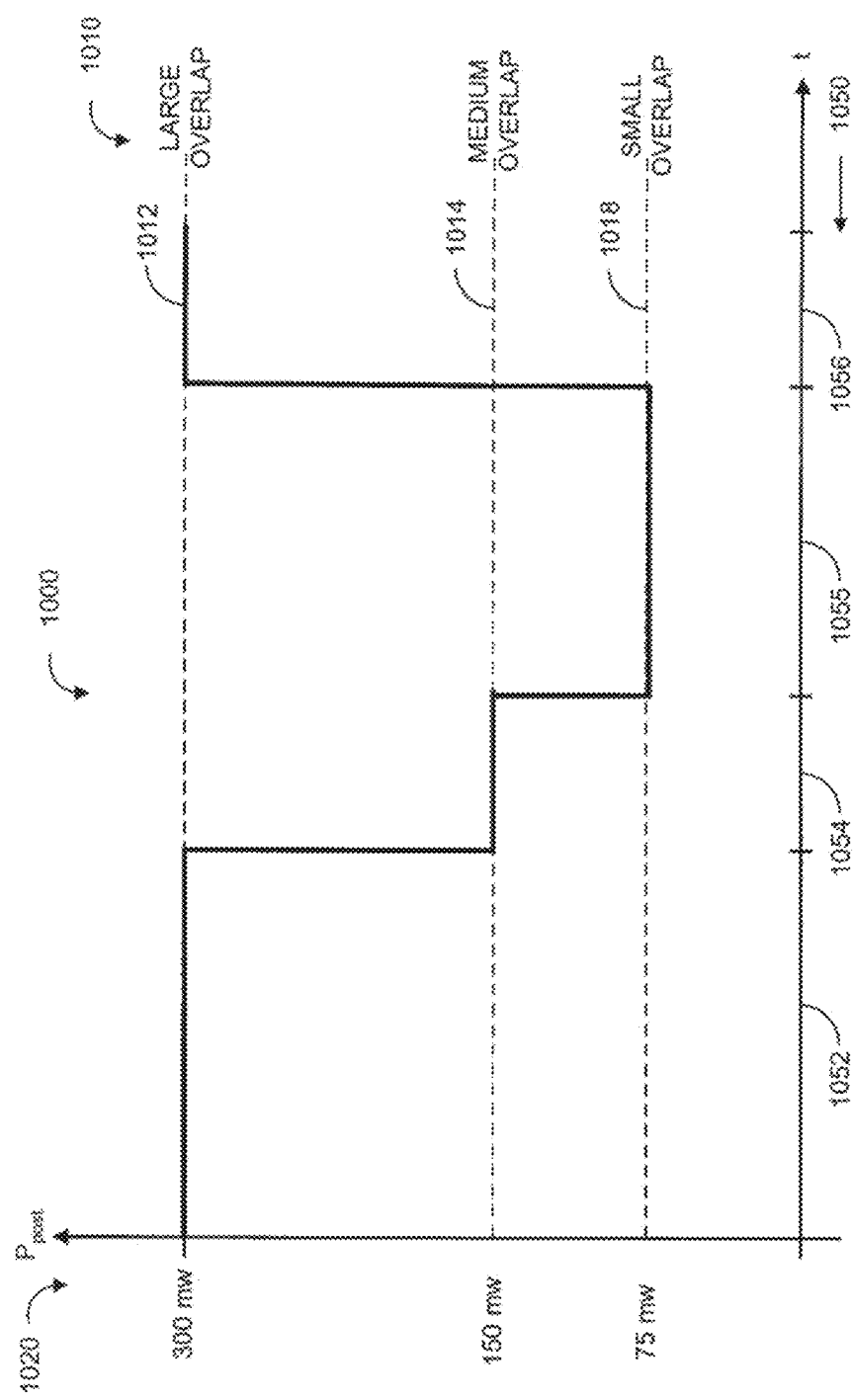
FIG. 10 is a graph of power versus time illustrating power dissipation using variable data block overlap processing.

FIG. 10 illustrates an exemplar power consumption versus time profile 1000 for the post processor 430 (FIG. 4) during various control engine states. In one embodiment, the control engine 440 (FIG. 4) has three states related to the sampling control output 366 (FIG. 4) that affect post processor power consumption accordingly. One of ordinary skill in the art will recognize that the control engine may have greater or fewer states and associated power consumption levels. The profile 1000 shows the three control engine states 1010 and the associated post processor power consumption levels 1020. These three states are large overlap 1012, medium overlap 1014 and small overlap 1018.

As shown in FIG. 10, in the large overlap state 1012, the control engine 440 (FIG. 4) causes the post processor to process data blocks that have a comparatively small time shift 706 (FIG. 7A), and the post processor exhibits relatively high power consumption under these conditions, say 300 mw. In the medium overlap state 1014, the control engine 440 (FIG. 4) causes the post processor to process data blocks that have a comparatively larger time shift 706 (FIG. 7A). For example, the data blocks may be time shifted twice as much as for the large overlap state 1012, and, as such, the post processor performs only half as many computations and consumes half the nominal power, say 150 mw. In the small overlap state 1018, the control engine 440 (FIG. 4) causes the post processor to process data blocks that have a comparatively large time shift. For example, the data blocks may be time shifted twice as much as for the medium overlap state 1014. As such, the post processor performs only a quarter as many computations and consumes a quarter of the nominal power, say 75 mw, as for the large overlap state 1012. In one embodiment, the control engine 440 (FIG. 4) alters the data block overlap of the post processor in conjunction with the duty cycle of the emitter drivers described with respect to FIG. 5, above, and the front-end sampling described with respect to FIG. 6, above, so that the average power consumption of the pulse oximeter matches a target level indicated by the power status output 462 (FIG. 4) or so that the power consumption is otherwise reduced or minimized.

In a preferred embodiment, data blocks are time shifted by either about 0.4 sec or about 1.2 sec, depending on the overlap state of the control engine 440 (FIG. 4). In a more preferred embodiment, the data blocks are varied between about 1.2 sec and about 4.8 sec. In a most preferred embodiment, the data blocks are time shifted by either about 1.2 sec, about 2.4 sec or about 4.8 sec, depending on the overlap state of the control engine 440 (FIG. 4). Although the post-processing of data blocks is described above with respect to only a few overlap states and a corresponding number of particular data block time shifts, there may be many overlap states and a corresponding range of data block time shifts.

Further shown in FIG. 10, power consumption 1020 changes according to the control states 1010 during each of the time intervals 1050. In a first time interval 1052, the post processor is in a large overlap state 1012 and transitions to a medium overlap state 1014 during a second time interval 1054, so as to meet a power target during a high signal quality period, for example. During a third time interval 1055, the post processor enters a small overlap state 1018, for example to meet a power target by further reducing power consumption. In a forth time interval 1056, the post processor transitions back to a large overlap state 1012, such as during an event or low signal quality conditions.

Figure 11:
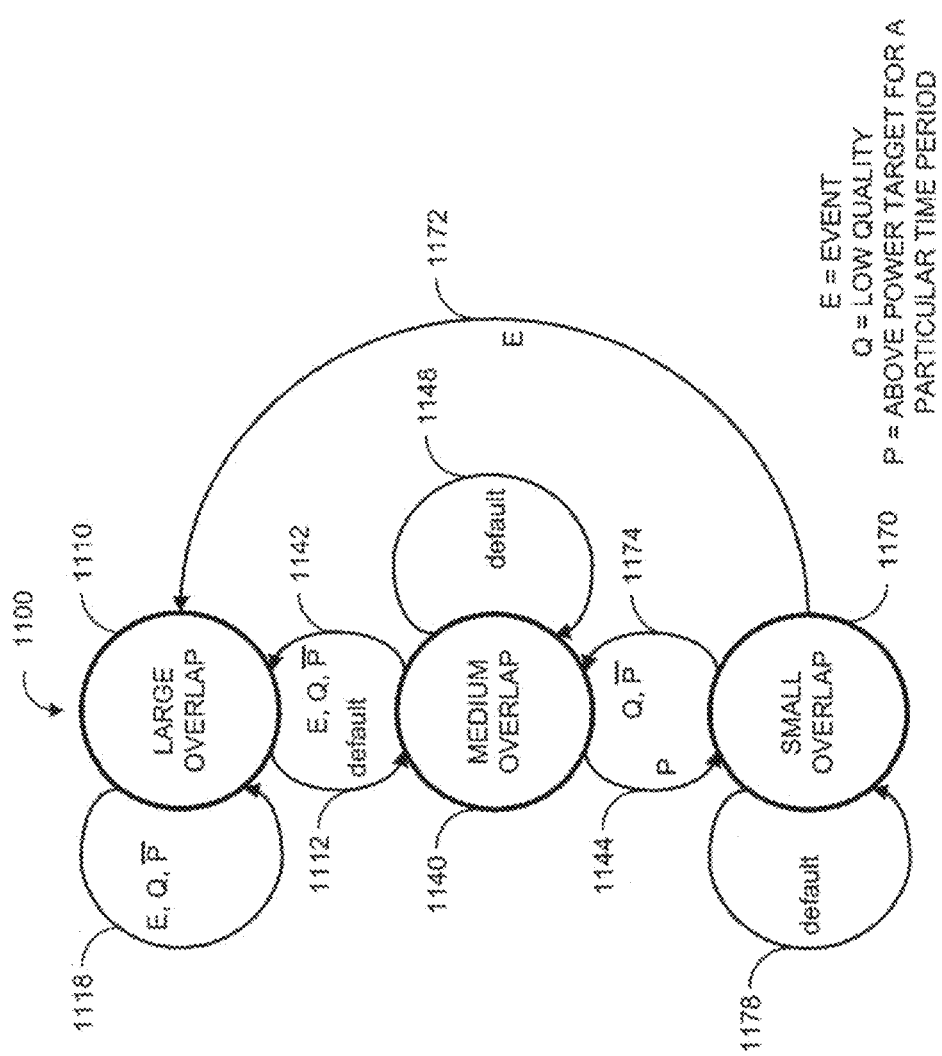
FIG. 11 is a state diagram of the sampling controller for variable data block overlap processing.

FIG. 11 illustrates a state diagram 1100 for one embodiment of the control engine 440 (FIG. 4). These states may function in parallel with, or in combination with, the sampling states described with respect to FIG. 9, above. In the illustrated embodiment, there are three control states, large overlap 1110, medium overlap 1140 and small overlap 1170, as described with respect to FIG. 10, above. If the control state is small overlap 1170, an event triggers a small overlap to large overlap transition 1172. If the control state is medium overlap 1140, an event similarly triggers a medium overlap to large-overlap transition 1142. In this manner, the occurrence of an event initiates the processing of more data blocks, allowing more robust signal statistics and higher fidelity monitoring of the event. Similarly, if the control state is medium overlap 1140, low signal quality triggers a medium overlap to large overlap transition 1142. In this manner, low signal quality initiates the processing of more data blocks, providing more robust signal statistics during lower signal-to-noise ratio periods.

Also shown in FIG. 11, if the control state is large overlap 1110 and either an event is occurring or signal quality is low, then a null transition 1118 maintains the large overlap state 1110. If the pulse oximeter is not above the power target for more than a particular time interval, a null transition 1148 maintains the medium overlap state 1140, so that reduced data processing occurs only when necessary to track the power target. Further, if the control state is small overlap 1170, a null transition 1178 maintains this power saving state until the power target is reached or an event or low signal quality condition occurs.

In addition, FIG. 11 shows that when the control state is in a large overlap state 1110, if neither an event nor low signal quality are occurring, then a large overlap to medium overlap transition 1112 occurs by default. Also, if the control state is medium overlap 1140, if the power consumption is above the target level for longer than a particular time interval and no low signal quality condition or event is occurring, a medium overlap to small overlap transition 1174 occurs, allowing power consumption to come down to the target level. Further, if the control state is small overlap 1170, if no event occurs but the power target has been met, a small overlap to medium overlap transition 1174 occurs.

A low power pulse oximeter embodiment is described above as having a power status calculator 460 (FIG. 4) and an associated power target. Another embodiment of a low power pulse oximeter, however, functions without either a power status calculator or a power target, utilizing the sampling controls 362, 364, 366 (FIG. 3) in response to internal parameters and/or output parameters, such as signal statistics 344 (FIG. 3) and/or physiological measurements 342 (FIG. 3) to reduce power consumption except during, say, periods of low signal quality and physiological events.

One of ordinary skill in the art will recognize that various state diagrams are possible representing control of the emitter drivers, the detector front-end and the post-processor. Such state diagrams may have fewer or greater states with differing transitional characteristics and with differing relationships between sampling mechanisms than the particular embodiments described above. In relatively simple embodiments of the control engine 440 (FIG. 4), only a single sampling mechanism is used, such as the sampling mechanism used to vary the duty cycle of the emitter drivers. The single sampling mechanism may be based only upon internal parameters, such as signal quality, only upon output parameters, such as those that indicate the occurrence of physiological events, or upon a combination of internal and output parameters, with or without a power target.

In relatively more complex embodiments of the control engine 440 (FIG. 4), sampling mechanisms are used in combination. These sampling mechanisms may be based only upon internal parameters, only upon output parameters, or upon a combination of internal and output parameters, with or without a power target. In a particular embodiment, the emitter duty-cycle, front-end duty-cycle and data block overlap sampling mechanisms described above are combined. A "reduced overlap" state relating to the post-processing of data blocks is added to the diagram of FIG. 9 between the "low duty cycle" state and the "data off" state. That is, sampling is varied between a high duty cycle state, a low duty cycle state, a reduced overlap state and a data off state in response to signal quality and physiological events, with or without a power target.

The low power pulse oximeter has been disclosed in detail in connection with various embodiments. These embodiments are disclosed by way of examples only and are not to limit the scope of the claims that follow. One of ordinary skill in the art will appreciate many variations and modifications.

What is claimed is:

1. A method of operating a patient monitor configured to monitor at least a pulse rate of a patient by processing signals responsive to light attenuated by body tissue, the method comprising:
   operating the patient monitor according to a first control protocol, wherein said operating includes activating a first control protocol light source in accordance with the first control protocol, the first control protocol light source including one or more of a plurality of light sources;
   when operating according to the first control protocol, calculating, by the patient monitor, measurement values of the pulse rate, the measurement values responsive to light from the first control protocol light source, detected by a detector of an optical sensor after attenuation by body tissue of the patient using the patient monitor;
   generating a trigger signal, wherein generating said trigger signal is responsive to at least one of: a comparison of processing characteristics to a predetermined threshold, a physiological event, or signal quality characteristics of signals received from the detector;
   in response to receiving the trigger signal, operating the patient monitor according to a second control protocol different from the first control protocol, wherein said operating includes activating a second control protocol light source in accordance with the second control protocol, the second control protocol light source including one or more of the plurality of light sources; and
   when operating the patient monitor according to the second control protocol, calculating the measurement values of the pulse rate, the measurement values responsive to light from the second control protocol light source, detected by the detector after attenuation by the body tissue of the patient using the patient monitor,
   wherein said operating of the patient monitor according to the first control protocol operates the first control protocol light source according to a first duty cycle and said operating of the patient monitor according to the second control protocol operates the second control protocol light source according to a second duty cycle, wherein power consumption of the first control protocol light source according to the first duty cycle is different than power consumption of the second control protocol light source according to the second duty cycle.

2. The method of claim 1, wherein the first control protocol light source operates on the first duty cycle having an active time and an inactive time according to the first control protocol, wherein the second control protocol light source operates on the second duty cycle having an active time and an inactive time according to the second control protocol, the active time of the first duty cycle having a first duration and the active time of the second duty cycle having a second duration, wherein the first duration and the second duration are different.

3. The method of claim 2, wherein the second duration is longer than the first duration.

4. The method of claim 1, wherein power consumption during said operating at the second control protocol is greater than power consumption during said operating at the first control protocol.

5. The method of claim 1, wherein said operating the patient monitor according to the first control protocol consumes a relatively small amount of power, and wherein said operating the patient monitor according to the second control protocol consumes a relatively large amount of power.

6. The method of claim 1, wherein said operating the patient monitor in accordance with the first control protocol comprises operating the first control protocol light source in a data off state.

7. The method of claim 1, wherein said signals received from the detector are responsive to the detected light of the first control protocol light source or the second control protocol light source.

8. The method of claim 7, wherein the signal quality characteristics includes at least one of signal strength, a presence of noise, or a presence of motion induced noise.

9. The method of claim 1, wherein the physiological event includes at least one of oxygen desaturation, an abnormal pulse rate, or an abnormal plethysmograph waveform.

10. The method of claim 9, wherein the physiological event includes the abnormal pulse rate and wherein the abnormal pulse rate includes an elevated pulse rate.

11. A patient monitor configured to monitor at least a pulse rate of a patient by processing signals responsive to light attenuated by body tissue, the patient monitor comprising:
    a plurality of light sources;
    at least one detector of an optical sensor configured to receive light after attenuation by body tissue of the patient using the patient monitor; and one or more processors configured to:

operate the patient monitor according to a first control protocol, wherein said operating includes activating a first control protocol light source in accordance with the first control protocol, the first control protocol light source including one or more of said plurality of light sources;

when operating according to the first control protocol, calculate, by the patient monitor, measurement values of the pulse rate, the measurement values responsive to light from the first control protocol light source, detected by said at least one detector after attenuation by the body tissue of the patient using the patient monitor;

generate a trigger signal, wherein generation of said trigger signal is responsive to at least one of: a comparison of processing characteristics to a predetermined threshold, a physiological event, or signal quality characteristics of signals received from the detector;

in response to receiving the trigger signal, operate the patient monitor according to a second control protocol different from the first control protocol, wherein said operation includes activating a second control protocol light source in accordance with the second control protocol, the second control protocol light source including one or more of said plurality of light sources; and when operating the patient monitor according to the second control protocol, calculate the measurement values of the pulse rate, the measurement values responsive to light from the second control protocol light source, detected by said at least one detector after attenuation by the body tissue of the patient using the patient monitor, wherein said operation of the patient monitor according to the second control protocol operates the first control protocol light source according to a first duty cycle and said operation of the patient monitor according to the second control protocol operates the second control protocol light source according to a second duty cycle, wherein power consumption of the first control protocol light source according to the first duty cycle is different than power consumption of the second control protocol light source according to the second duty cycle.

12. The patient monitor of claim 11, wherein said operation of the first control protocol light source on the first duty cycle has an active time and an inactive time according to the first control protocol, wherein said operation of the second control protocol light source on the second duty cycle has an active time and an inactive time according to the second control protocol, wherein the active time of the first duty cycle has a first duration and the active time of the second duty cycle has a second duration, wherein the first duration and the second duration are different.

13. The patient monitor of claim 12, wherein the second duration is longer than the first duration.

14. The patient monitor of claim 11, wherein power consumption during said operation at the second control protocol is greater than power consumption during said operation at the first control protocol.

15. The patient monitor of claim 11, wherein said operation of the patient monitor in accordance with the first control protocol comprises operating the first control protocol light source in a data off state.

16. The patient monitor of claim 11, wherein said signals received from the detector are responsive to the detected light of the first control protocol light source or the second control protocol light source.

* * * * *

UNITED STATES PATENT AND TRADEMARK OFFICE
CERTIFICATE OF CORRECTION

PATENT NO. : 10,433,776 B2
APPLICATION NO. : 16/174144
DATED : October 8, 2019
INVENTOR(S) : Ammar Al-Ali Page 1 of 1

It is certified that error appears in the above-identified patent and that said Letters Patent is hereby corrected as shown below:

In the Specification

In Column 8 at Line 40, change "forth" to --fourth--.

In Column 10 at Line 15, change "forth" to --fourth--.

In the Claims

In Column 13 at Line 36, in Claim 11, change "second control protocol" to --first control protocol--.

Signed and Sealed this
Tenth Day of November, 2020

Andrei Iancu
*Director of the United States Patent and Trademark Office*